US008002548B2

(12) United States Patent
Lee

(10) Patent No.: US 8,002,548 B2
(45) Date of Patent: Aug. 23, 2011

(54) METHOD OF MAXILLARY SINUS BONE GRAFTING FOR PLACEMENT OF IMPLANT

(76) Inventor: Dal Ho Lee, Seoul (KR)

( * ) Notice: Subject to any disclaimer, the term of this patent is extended or adjusted under 35 U.S.C. 154(b) by 155 days.

(21) Appl. No.: 12/465,313

(22) Filed: May 13, 2009

(65) Prior Publication Data

US 2010/0291511 A1 Nov. 18, 2010

(51) Int. Cl.
*A61F 2/02* (2006.01)
(52) U.S. Cl. .................................... 433/173; 623/17.17
(58) Field of Classification Search ................. 433/173, 433/174; 623/17, 17.17
See application file for complete search history.

(56) References Cited

U.S. PATENT DOCUMENTS

| | | | | |
|---|---|---|---|---|
| 5,711,315 | A * | 1/1998 | Jerusalmy | 128/898 |
| 7,510,397 | B2 * | 3/2009 | Hochman | 433/172 |
| 2006/0204929 | A1 * | 9/2006 | Kitamura et al. | 433/173 |
| 2006/0275738 | A1 * | 12/2006 | Flanagan | 433/215 |
| 2008/0161934 | A1 * | 7/2008 | Yamada | 623/17.17 |
| 2009/0004624 | A1 * | 1/2009 | Lee | 433/144 |
| 2009/0181345 | A1 * | 7/2009 | Kfir | 433/172 |
| 2009/0258328 | A1 * | 10/2009 | Chen | 433/173 |
| 2009/0259227 | A1 * | 10/2009 | Ahn | 606/80 |
| 2009/0274996 | A1 * | 11/2009 | Miller | 433/215 |
| 2009/0326440 | A1 * | 12/2009 | Lee | 604/22 |
| 2010/0042222 | A1 * | 2/2010 | Song | 623/17.17 |
| 2010/0081111 | A1 * | 4/2010 | Better et al. | 433/174 |
| 2010/0178631 | A1 * | 7/2010 | Wallis et al. | 433/82 |
| 2010/0196841 | A1 * | 8/2010 | Nahlieli et al. | 433/29 |
| 2010/0255444 | A1 * | 10/2010 | Karmon | 433/172 |
| 2010/0255446 | A1 * | 10/2010 | Better et al. | 433/174 |

OTHER PUBLICATIONS

Krennmair, G. et al., Maxillary Sinus Lift for Single Implant-Supported Restorations: A Clinical Study, Int J Oral Maxillofac Implants, May-Jun. 2007; 22(3): 351-8, Abstract.
Ferrigno, N. et al., Dental Implants Placement in Conjunction with Osteotome Sinus Floor Elevation: A 12-year Life-Table Analysis from a Prospective Study on 588 ITI Implants, Clin. Oral Implants Res., Apr. 2006; 17(2): 194-205, Abstract.
Fugazzotto, PA, Sinus Floor Augmentation at the Time of Maxillary Molar Extraction: Technique and Report of Preliminary Results, Int J Oral Maxillofac Implants, Jul.-Aug. 1999; 14(4):536-42, Abstract.
Katranji, A. et al., Sinus Augmentation Complications: Etiology and Treatment, Implant Dent., Sep. 2008; 17 (3):339-49, Abstract.
Jurisic, M. et al., Maxillary Sinus Floor Augmentation: Comparing Osteotome with Lateral Window Immediate and Delayed Implant Placements. An interim report, Oral Surg Oral Med Oral Pathol Oral Radiol Endod., Dec. 2008; 106 (6): 820-7, Epub Jul. 7, 2008, Abstract.

(Continued)

*Primary Examiner* — Ralph A Lewis
(74) *Attorney, Agent, or Firm* — Galgano & Associates, PLLC; Thomas M. Galgano; Jessica G. Bower

(57) ABSTRACT

A method of maxillary sinus bone grafting for placement of an implant in which upon placement of the implant, a vertical hole is formed and enlarged with ease in a maxillary sinus floor, a maxillary membrane is easily lifted in an always-stable state using a piezotome and gel type bone graft material while preventing the membrane from becoming damaged, and even the bone graft material of coarse bone meal is uniformly diffused and infused, thereby ensuring that the implant is placed in a fast, safe manner while allowing a patient to keep relaxed and alleviating the pain the patient feels, resulting in shortening a curing time and maximizing effects of the placement of the implant.

11 Claims, 15 Drawing Sheets

OTHER PUBLICATIONS

Fermergard, R. et al., Osteotome Sinus Floor Elevation and Simultaneous Placement of Implants- A 1-year Retrospective Study with Astra Tech Implants, Clin Implant Dent Relat Res., Mar. 2008; 10(1):62-9, Abstract.

Wallace, SS. et al., Schneiderian Membrane Perforation Rate During Sinus Elevation Using Piezosurgery: Clinical Results of 100 Consecutive Cases, Int J Periodontics Restorative Dent., Oct. 2007; 27(5):413-9, Abstract.

Chen, TW. et al., Implant Placement Immediately After the Lateral Approach of the Trap Door Window Procedure to Create a Maxillary Sinus Lift without Bone Grafting: A 2-year Retrospective Evaluation of 47 Implants in 33 Patients, J Oral Maxillofac Surg., Nov. 2007; 65(11):2324-8, Abstract.

Wallace, SS. et al., Sinus Augmentation Utilizing Anorganic Bovine Bone (Bio-Oss) with Absorable and Nonabsorable Membranes Placed over the Lateral Window: Histomorphometric and Clinical Analyses, Int J Periodontics Restorative Dent., Dec. 2005; 25(6):551-9, Abstract.

Peleg, M. et al., Sinus Floor Augmentation with Simultaneous Implant Placement in the Severely Atrophic Maxilla, J Periodontol, Dec. 1998; 69(12):1397-403, Abstract.

* cited by examiner

METHOD OF MAXILLARY SINUS BONE GRAFTING FOR PLACEMENT OF IMPLANT

BACKGROUND OF THE INVENTION

1. Field of the Invention

The present invention relates to a method of maxillary sinus bone grafting for implant placement by which an artificial tooth is effectively placed into the mouth of a patient, and more particularly, to a method of maxillary sinus bone grafting for implant placement by which an implant can be implanted in a fast, safe manner while allowing a patient to stay relaxed, resulting in maximizing effects of the placement.

2. Description of the Related Art

While an implant generally refers to replacement of a specific section of a human body, it means grafting of an artificial tooth in dentistry. The implant is a hi-tech operation method by which upon the occurrence of the loss of the root of a tooth, an artificial dental root made of titanium, which is not rejected by the human body, is implanted in the alveolus from which the tooth was removed, and an artificial tooth then is fixed thereto to recover an original function of the tooth. In comparison with a common prosthesis or denture, which causes the neighboring teeth and bone to be damaged as time passes, the implant has advantages in that it does not have a bad influence on the neighboring teeth, and that it is usable for a long time since it prevents tooth decay while being of similar function and shape to that of the natural tooth.

However, since many of the patients have an oral structure in which is difficult to place an implant, some of dentists tend to avoid treating such patients. Particularly, it was reported that the success rate of implants at the upper posterior teeth was comparatively lower than that for other areas. This is because the upper posterior teeth are weak and the maxillary sinus exists near the upper posterior teeth, so that a long implant cannot be placed into the upper posterior teeth.

That is, since the maxillary sinus existing in the maxillary is a space surrounded by a mucous membrane, when a tooth is lost, the maxillary sinus physiologically falls down and widens greatly and the downward extension of the maxillary sinus and the osteolysis owing to the loss of teeth occur, resulting in a lack in the amount of bone into which the implant can be placed, making it difficult to carry out the implantation for the upper posterior teeth.

Meanwhile, as a representative operating method of the related art in the case of the occurrence of a lack in the amount of bone up to the maxillary sinus, the two operating methods are as follows: a lateral window technique in which a lateral window is formed below a malar bone, a maxillary membrane is directly lifted therethrough, and a graft material is filled between the inferior margin of the maxillary sinus and the maxillary membrane; and a crestal approach technique using an osteotome.

First, the lateral window technique is an operating method for the placement of a long implant at the location of a maxillary posterior tooth, which is greatly deficient in the amount of bone in a vertical direction (remaining bone is 5 mm or less), wherein the method is carried out so that a sidewall of a maxillary is removed in consideration of the height of the remaining maxillary extending up to the maxillary sinus, and the amount of bone is secured through bone grafting.

In detail, the lateral window technique includes a process of harvesting bone fragments of a patient in order to graft a bone to a portion where the amount of a bone is deficient from a bone section other than the section to be operated on (if it is difficult to harvest bone fragments from the patient, artificial bone is used), a setting process of creating an incision line to a vestibular region of a section corresponding to a molar tooth, a forming process of forming a mucoperiosteal flap, a windowing process of windowing a facial wall of maxillary sinus through a fracture line formed using a round bur, a piezo sawtooth, or a diamond tip, after windowing, a lifting process of lifting the facial wall of the maxillary sinus and a membrane of the maxillary sinus, a treating process of treating a space in the maxillary sinus whose bone plate was lifted, a grafting process of grafting a bone, a suturing process, and a placement process of implanting an implant 6 to 12 months after the operation.

However, such a lateral window technique is very difficult to do and is a careful, time-intensive process because especially during the windowing the maxillary sinus is often punctured in the process of using the round bur, the piezo sawtooth, or the diamond tip, resulting in the symptoms of swelling and pain.

Further, the crestal approach method is an operating method implemented when the amount of remaining bone is slightly deficient (e.g. 5 to 10 mm), wherein a bone is lifted using a chisel such as an osteotome, or the sinus floor is removed using a special drill or reamer, an autogenous bone or an artificial bone is grafted into that space and an implant is placed there.

That is, the crestal approach technique is carried out so that a hole is formed using a drill at a portion where an implant is placed, osteotomes (each having diameters ranging in size from small to large) are inserted in a series into the hole and are hammered so as to gradually enlarge the hole, approach the maxillary membrane so as to fracture only bone without damaging the membrane, an autogenous bone or an artificial bone is grafted in that space, and the implant is placed there.

In detail, the crestal approach includes a process of forming the hole using a twist drill extending to a stable distance which does not however reach the maxillary membrane, i.e. up to a compact bone below the maxillary membrane, a process of sequentially inserting and hammering the osteotomes having diameters varying from a small size to a large size into the hole so as to form a hole corresponding to a diameter of the implant, and upon formation of the hole suitable to implant placement, a process of finally and carefully hammering the osteotome so as to fracture the compact bone, a process of filling the hole of the compact bone with a bone graft material, a process of softly hammering the osteotome into the hole filled with the bone graft material so as to lift the maxillary membrane, and then a process of removing the sinus floor using the special drill or reamer, a process of lifting the maxillary membrane using the graft material until a height of available bone is secured such that the implant can be placed through that height, and a process of placing the implant.

However, despite that such a crestal approaching technique has the advantage of few occurrences of edema occurring in patients after operation because of the narrow target section of the operation, a long time is spent performing the operation since a dentist cannot directly observe the maxillary membrane so that he must operate very carefully while checking the target section using X-rays, a patient feels very unpleasant owing to the striking which is done during the operation, and particularly when the drill comes into point contact with the maxillary membrane as the tip thereof rotates is a vertical load concentrated upon the contacted maxillary membrane thereby easily fracturing the same.

That is, while the special drill or reamer does not fracture the sinus floor of the maxillary membrane since it is not hammered (so that it causes only a little pain to the patient), it has a very small operating force so as to be insufficient to puncture the maxillary membrane, so that it takes too long of a time to remove the same. Further, if the maxillary membrane is of an irregular shape or is severely inclined, the drill or reamer can puncture the maxillary membrane while removing the sinus floor, making it difficult to maintain in place the bone graft material for forming the bone material. This allows the implant to be exposed to the outside in the maxillary membrane without being placed in the bone, thereby increasing the possibility of infection and degrading the capability of supporting the implant because of an insufficient amount of support bone.

Therefore, recently there has been proposed a piezoelectric device which has been known to comparatively advantageously protect the weak maxillary membrane upon the formation of a window or the lifting of the maxillary membrane because unlike the existing method, it hardly punctures or tears the maxillary membrane even when coming into contact with the same.

However, carrying out the placement of an implant using such a conventional piezoelectric device has problems in that even experienced dentists in performing the placement find it difficult to lift the maxillary membrane in an always-safe state without damaging it, and in that in case of puncturing the vertical hole into which the implant is placed, a narrow drill should be used, and in that while in the process of placing the bone graft material into the section of the root of the artificial tooth, the bone graft material is placed into the section while being loaded in a bone carrier, in case of using the bone carrier, a tip size of a protrusion in front of a syringe barrel thereof is too large or small for the punctured hole, so that during injection the bone graft material escapes outside or is not uniformly dispensed into the hole to a sufficient depth.

Particularly, in case of the placement of the bone graft material into an upper molar using a common syringe, problems arise because inconvenience is caused by the placement, a lot of time is required for the placement, the placement is difficult to carry out and thus efficient placement cannot be implemented in an easy state, and because of the unnatural forcible placement, whereby if the bone graft material is of coarse particles, the graft and lifting become difficult owing to the roughness of the particles, which may cause the maxillary membrane and also the gums to be damaged, and further because although coarse bone meal is effectively used in the placement of the bone graft material rather than fine bone meal, such coarse bone meal cannot be used in common syringes. Therefore, there is a need for a method for placing an implant by which the implant can be put in place in a fast, safe manner while allowing a patient to keep relaxed and alleviating the pain the patient feels, resulting in shortening a curing time and maximizing effects of the placement of the implant.

SUMMARY OF THE INVENTION

Accordingly, the present invention has been made keeping in mind the above problems occurring in the related art, and the present invention is intended to propose a method of maxillary sinus bone grafting for placement of an implant in which upon placement of the implant, a vertical hole can be formed and enlarged with ease in a maxillary sinus floor, a maxillary membrane can be easily lifted in an always-stable state using a piezotome and gel type bone graft material while preventing the membrane from becoming damaged, and even the bone graft material of coarse bone meal can be uniformly diffused and infused, thereby ensuring that the implant is placed in a fast, safe manner while allowing a patient to keep relaxed and alleviating the pain the patient feels, resulting in shortening a curing time and maximizing effects of the placement of the implant.

In order to achieve the above object, according to one aspect of the present invention, there is provided a method of maxillary sinus bone grafting for placement of an implant, the method including: a first step of forming a vertical hole in a maxillary sinus floor of a maxillary sinus for placement of the implant; a second step of lifting a maxillary membrane via the vertical hole in the maxillary sinus floor; a third step of enlarging a diameter of the vertical hole with the maxillary membrane lifted; a fourth step of inserting the bone graft material via the enlarged vertical hole; a fifth step of pushing the inserted bone graft material in a space between the maxillary sinus floor and the maxillary membrane; and a sixth step of after the bone graft material has been cured, placing the implant into the vertical hole.

In an embodiment, in the first step, the maxillary sinus floor may be drilled using first and second bone compactors in turn.

In an embodiment, the first and second bone compactors may be of a diameter of 2.0 mm and 3.0 mm, respectively.

In an embodiment, the second step may include a first sub-step of primarily lifting the maxillary membrane via the vertical hole of the maxillary sinus floor and a second sub-step of filling gel type bone graft material between the maxillary sinus floor and the maxillary membrane, which has been primarily lifted via the vertical hole of the maxillary sinus floor, so as to secondarily lift the maxillary membrane.

In an embodiment, in the first sub-step, the lifting may be carried out using a piezotome, wherein the maxillary membrane is lifted by means of the pressure of water fed via the center of the piezotome.

In an embodiment, the piezotome may be provided on an outer circumference of a piezo pole thereof with a protruding stopper for restricting an insertion distance depending on a thickness of the maxillary sinus floor, so as to upon lifting, prevent a tip of the piezotome from excessively pushing up and damaging the maxillary membrane when being inserted into the maxillary sinus.

That is, while the piezotome is of an oscillating frequency of 20,000 Hz to 30,000 Hz and the oscillating movement is a slight movement so that it cannot tear the maxillary membrane, if after removing the bone, the tip of the piezotome is unintentionally pushed in the maxillary sinus by the dentist's mistake of regulating a manipulating force, the pushing movement may cause the maxillary membrane to be punctured and therefore a tip of a newly developed piezotome is provided with such a stopper in order to prevent the above problem.

In an embodiment, in the second sub-step, the lifting may be carried out using a bone infuser, first and second infuser bodies of which are detachably screwed in turn onto a leading end of a syringe barrel and which pushes the gel type bone graft material, which is filled in the bone infuser, between the maxillary sinus floor and the primarily lifted maxillary membrane so as to secondarily lift the maxillary membrane.

In an embodiment, in the third step, third to fifth bone compactors may be used to enlarge the vertical hole.

In an embodiment, the third to fifth bone compactors may be of a diameter of 3.8 mm, 4.0 mm, and 5.0 mm, respectively, to correspond to those of a common implant.

In an embodiment, in the fourth step, the inserting may be carried out using a bone infuser, first and second infuser bodies of which are detachably screwed in turn onto a leading end of a syringe barrel and which inserts granular bone graft material, which is filled in the bone infuser.

In an embodiment, the granular bone graft material may be of coarse or fine particles.

In an embodiment, in the fifth step, the granular bone graft material may be pushed up to an upper end of the vertical hole using a condenser.

According to the present invention, upon placement of the implant, the vertical hole can be formed and enlarged with ease in the maxillary sinus floor, the maxillary membrane can be easily lifted in an always-stable state using the piezotome and gel type bone graft material while preventing the membrane from becoming damaged, and even the bone graft material of coarse bone meal can be uniformly diffused and infused, thereby ensuring that the implant is placed in a fast, safe manner while allowing a patient to keep relaxed and alleviating the pain the patient feels, resulting in shortening a curing time and maximizing effects of the placement of the implant.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Description will now be made of exemplary embodiments of the present invention with reference to the accompanying drawings.

As illustrated in FIGS. 1 to 14, a method of maxillary sinus bone grafting for placement of an implant according to the present invention includes a first step of forming a vertical hole in a maxillary sinus floor of a maxillary sinus for placement of the implant, a second step of lifting a maxillary membrane via the vertical hole of the maxillary sinus floor, a third step of enlarging a diameter of the vertical hole with the maxillary membrane lifted, a fourth step of inserting the bone graft material via the enlarged vertical hole, a fifth step of pushing the inserted bone graft material in a space between maxillary sinus floor and the maxillary membrane, and a sixth step of after the bone graft material has been cured, placing the implant into the vertical hole.

Figure 1:
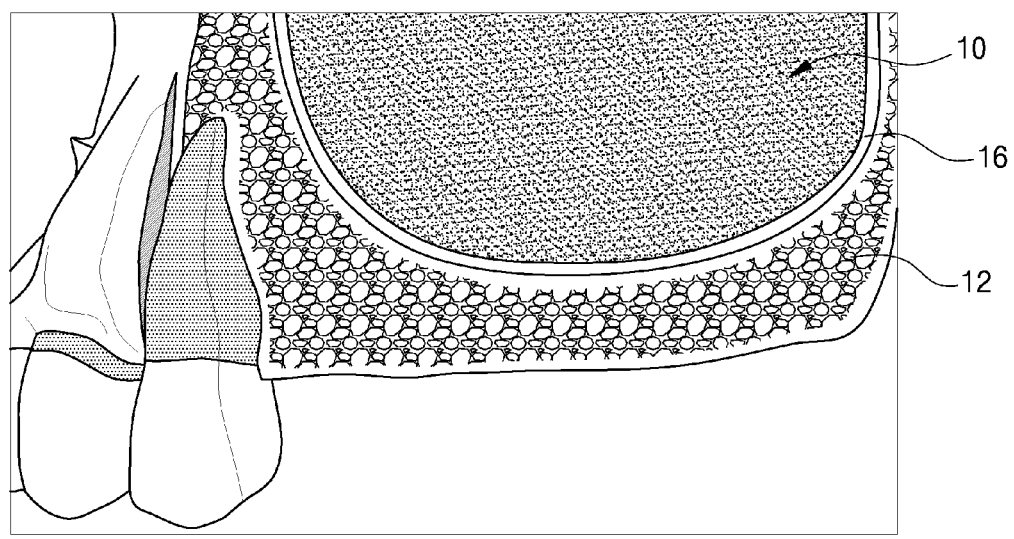
FIG. 1 is a cross-sectional view illustrating a maxillary sinus floor before placement of an implant according to the present invention.

First, in FIG. 1, upon placement of an implant in an upper posterior region, if a regular size implant (having a diameter of 4 mm or more and a length of 10 mm or more) is difficult to be placed owing to vertical bone deficiency in the upper posterior region, before the placement of an implant, bone grafting is generally carried out in order to thicken the corresponding region of a maxillary sinus floor.

In this process, a target region for the placement of the implant is first selected and radiographically evaluated so as to measure a thickness of a bone of the target region.

Figure 2:
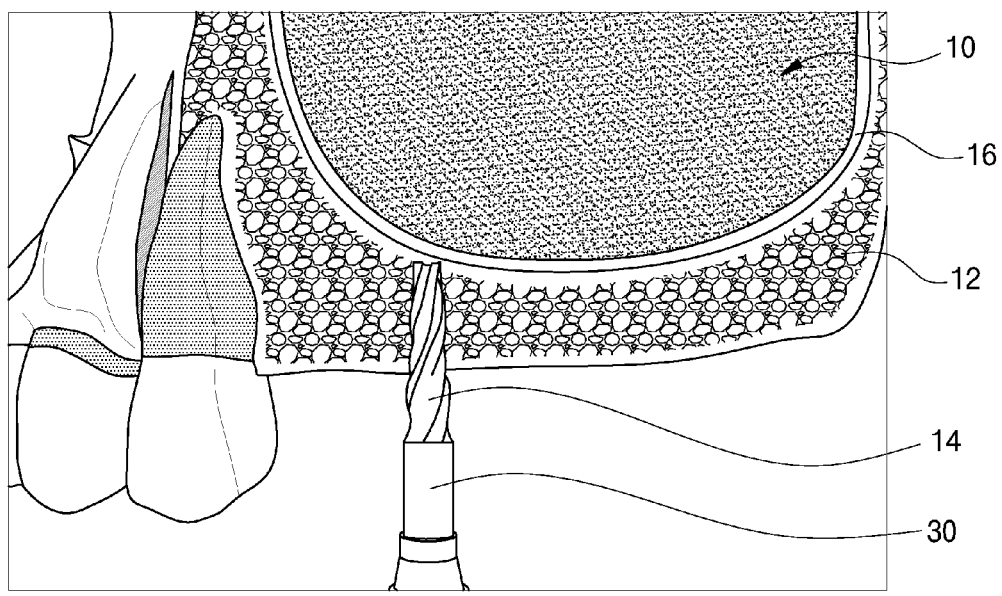
FIGS. 2 and 3 are cross-sectional views illustrating the process of forming a vertical hole in the maxillary sinus floor using first and second bone compactors.
Figure 3:
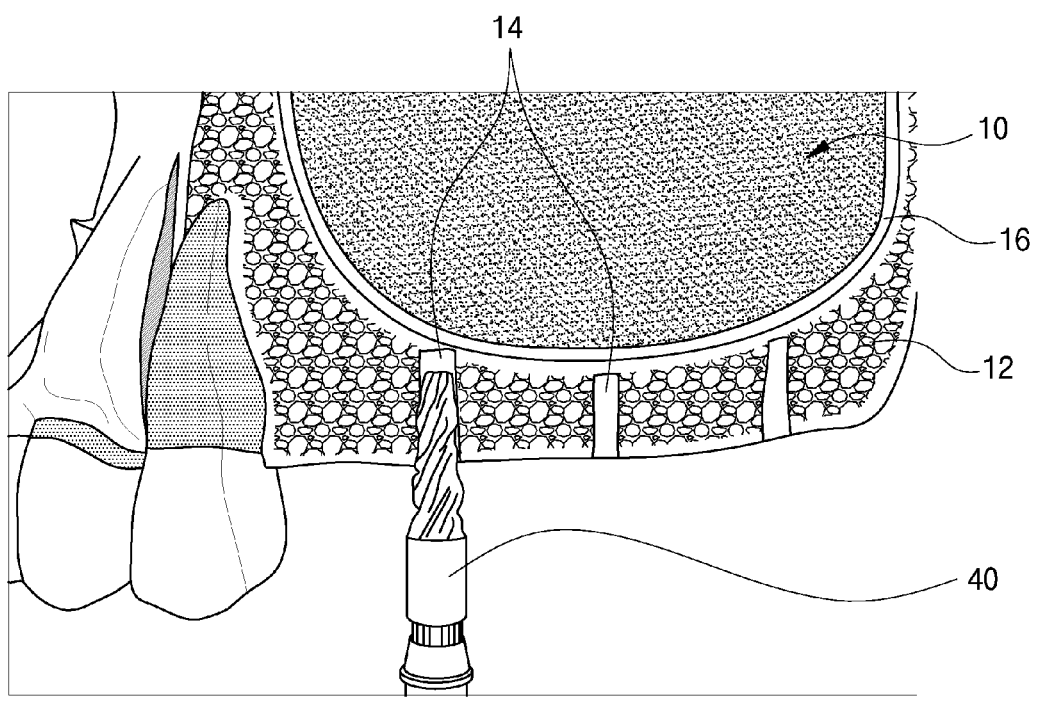

The steps of the bone grafting method of the invention are as follows: the first step is implemented such that a maxillary sinus floor 12 of a maxillary sinus is primarily drilled using a first bone compactor 30 having a diameter of 2.0 mm as illustrated in FIG. 2 and secondarily drilled on the primarily drilled portion using a second bone compactor 40 having a diameter of 3.0 mm as illustrated in FIG. 3, so as to form a vertical hole 14 in the maxillary sinus floor 12 for the placement of an implant 20.

Here, assuming that a thickness of a target bone for placement of an implant is Xmm, the vertical hole 14 is drilled up to X−1 mm, i.e., a region exactly before 1 mm from the thickness of the target bone, using the first and second bone compactors 30 and 40.

Figure 4:
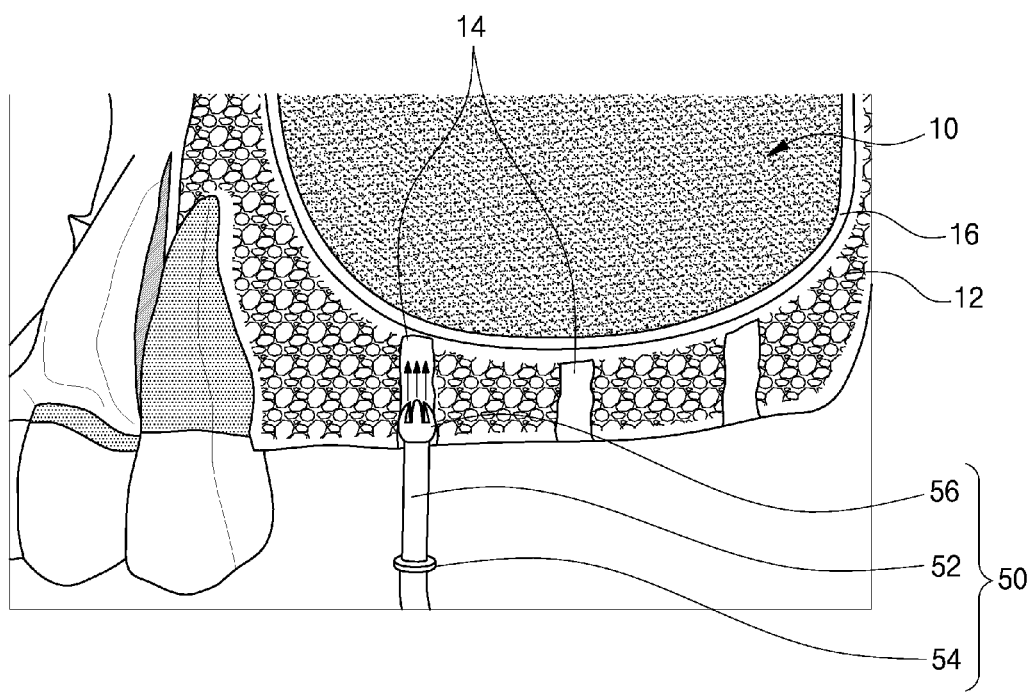
FIGS. 4 and 5 are cross-sectional views illustrating the process of primarily lifting a maxillary membrane using a piezotome.
Figure 5:
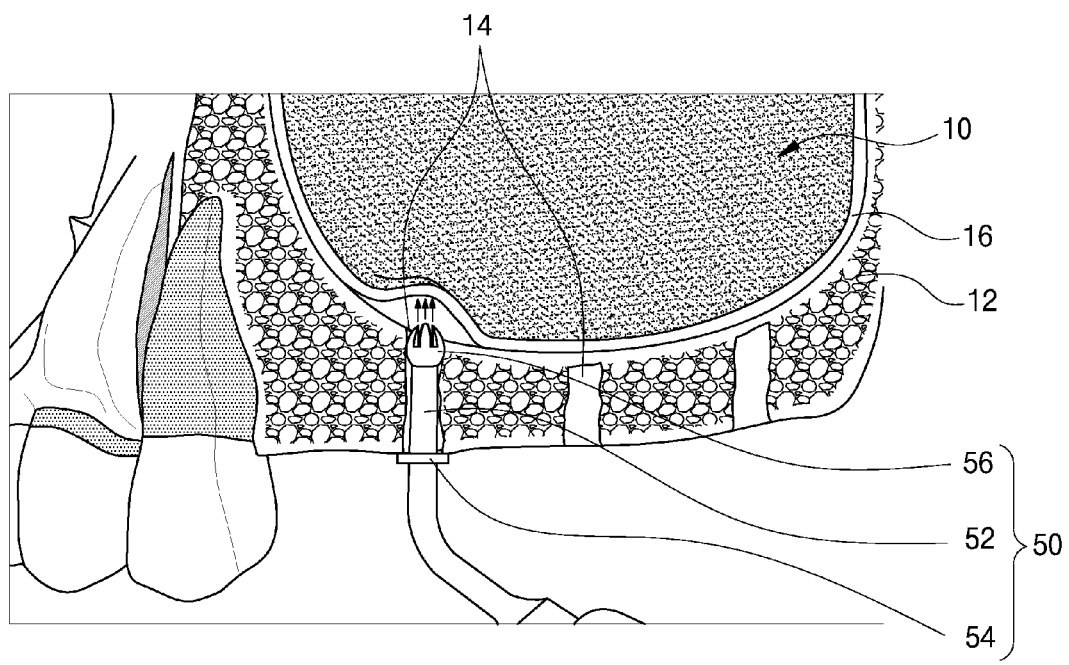

Next, in the second step, as illustrated in FIGS. 4 and 5, a maxillary membrane 16 is primarily lifted by means of pressure of water fed through a piezotome 50 while inserting the piezotome 50 via the vertical hole 14 formed in the maxillary sinus floor 12, the piezotome having a piezo tip of X+1 mm in which a stopper 54, which is disclosed in Korean patent application No. 10-2008-0060643 (Registration No. 0884211) and US Application No. 12313591, is formed on the outer circumference of a piezo pole 52. The stopper 54 protrudes from the outer circumference of the piezo pole 52 in order to restrict the insertion depth of the piezotome depending on the thickness of the maxillary sinus floor. Thus, the stopper effectively prevents the maxillary membrane 16 from being perforated owing to an excessive pushing motion of the piezo tip 56 into the maxillary sinus 10, so that the primary lifting of the maxillary membrane can be implemented in an always-stable manner.

Figure 6:
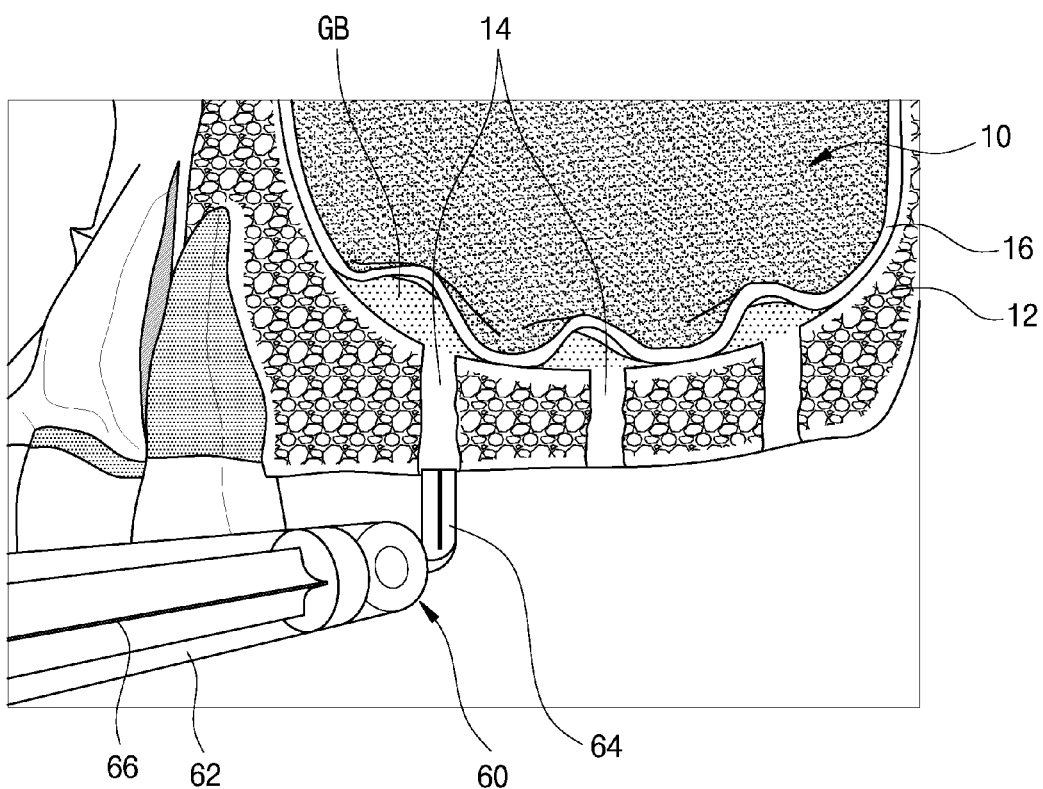
FIG. 6 is a cross-sectional view illustrating the process of secondarily lifting the maxillary membrane using the insertion of gel type bone graft material using a bone infuser.

Then, in the state of being primarily lifted as shown in FIG. 5, as shown in FIG. 6, a bone infuser 60, which is disclosed in Korean patent application No. 10-2008-0089717 by the applicant, and a body 64 of which is detachably screwed onto a leading end of a syringe barrel 62, is inserted via the vertical hole 14 of the maxillary sinus floor 12 and as a piston 66 is pushed in the syringe barrel, gel type bone graft material GB filled in the syringe barrel is infused into a gap of the primarily lifted maxillary membrane so as to secondarily lift the maxillary membrane. Then, the maxillary membrane 16 can be safely lifted without being torn, owing to proper liquidity and viscosity of the gel type bone graft material. The maxillary membrane may also be lifted in a horizontal state.

Here, if water is further injected so as to lift the maxillary membrane, a weak portion of the maxillary membrane 16 may be torn owing to the liquidity of water.

According to the conventional osteotome operating method, since the lifting is implemented using coarse granular bone graft material and the bone graft is done only in a vertical direction, the maxillary membrane 16 is easily torn, and the quantities of the graft bone material cannot be infused and thus the bone grafting is carried out only in the circumference of an implant so that if a prosthesis is mounted later and an occlusal force is loaded onto a target region, the amount of bone on the region is insufficient and the dental operation may fail. Therefore, such a conventional operating method is not used widely.

Figure 7:
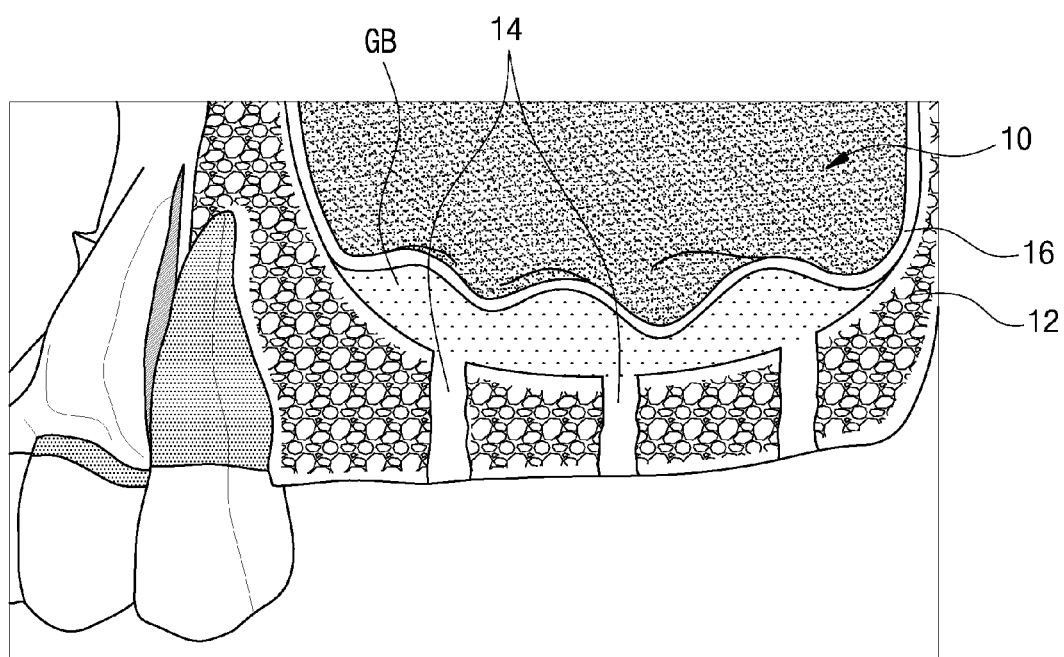
FIG. 7 is a cross-sectional view illustrating the state of having completed the secondary lifting shown in FIG. 6.
Figure 8:
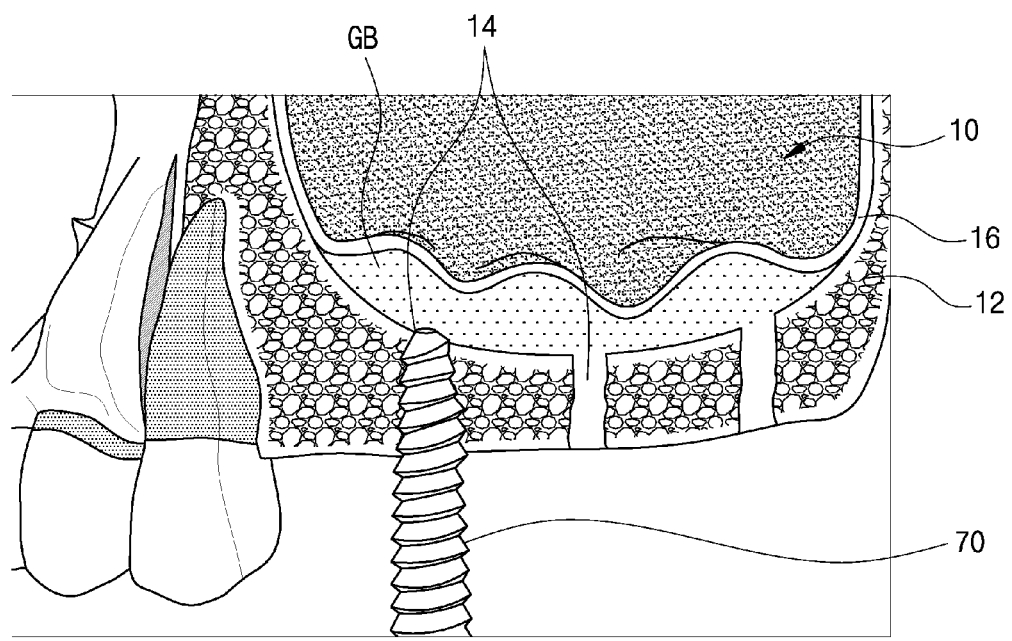
FIGS. 8 to 10 are cross-sectional views illustrating in series the process of enlarging a diameter of the vertical hole.
Figure 9:
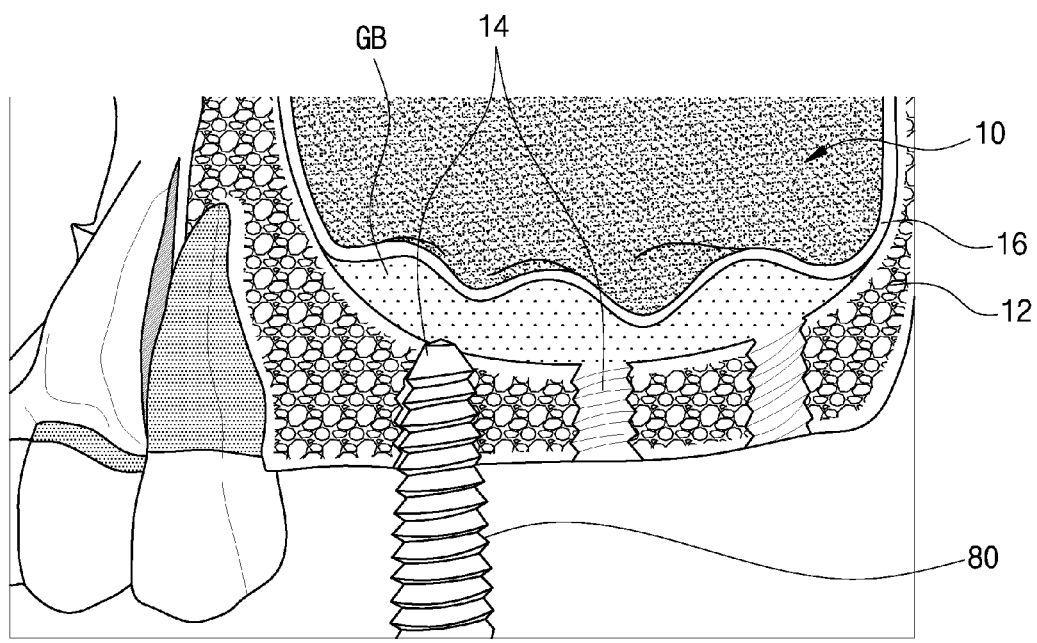
Figure 10:
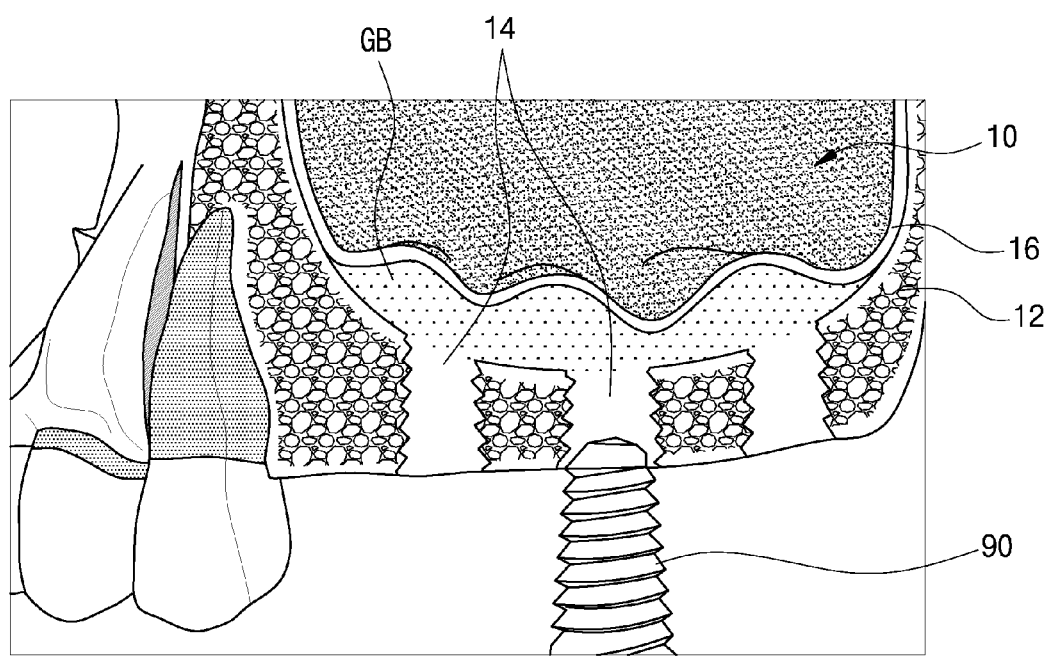

Next, in the third step, in the state as shown in FIG. 7 in which the gel type bone graft material GB is charged into the gap of the lifted maxillary membrane 16, as shown in FIGS. 8 to 10, the target region is expanded in diameter via the vertical hole 14 using in sequence third to fifth bone compactors 70, 80, and 90 having a diameter of 3.8 mm, 4.0 mm, and 5.0 mm, respectively, or spiral compactors or bone expanders.

When the diameter of the vertical hole 14 is expanded using a drill or bone compactor, the gel type bone graft material GB serves as a lubricant and a protector preventing the drill or the bone compactor from coming into direct contact with the maxillary membrane 16.

Meanwhile, if the bone density is divided into D1, D2, D3, and D4 categories, wherein the bone becomes stronger going towards D1 and weaker towards D4, in the bone of D4, upon implant placement, initial stability is hardly obtained, resulting in lowering the rate of success of the implant placement. The upper posterior generally has a density rating of D3 or D4.

Thus, in a case of low bone density, using the bone expander may be preferred, so that the vertical hole is increased in bone density and expanded in diameter.

However, in a case of a high bone density such as D1 or D2, if the bone compactor is used, owing to severe bone compression, a bone formation cell (osteoblast) may die or the bone may be broken, possibly resulting in failing of the implant placement. Thus, it is preferred that the diameter of the vertical hole be expanded using the shortest drill in an implant surgical drill kit.

Further, in a case where the maxillary sinus 10 is lifted after the vertical hole 14 is expanded to a desired final diameter (the regular size is 4 mm or more) as shown in FIG. 10, if an implant is placed later and a quantity of bone is grafted, granular bone graft material should be additionally grafted so that bone resorption is reduced.

Figure 11:
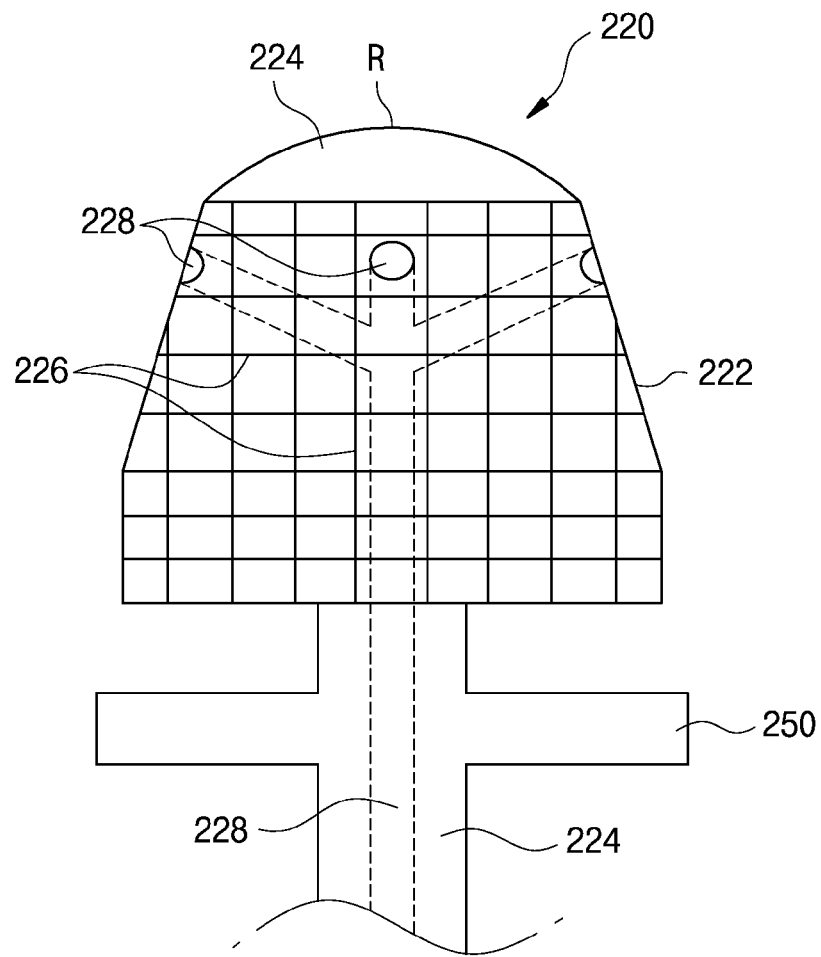
FIG. 11 is a front view illustrating a bone expander which may replace a drill.

Meanwhile, FIG. 11 is a front view illustrating a bone expander 220 which may replace a drill, which is disclosed in a Korean patent application by the applicant, and which is mounted on a hand piece of a piezo device in order to expand the vertical hole 14 of the maxillary sinus floor 12 for implant placement. The bone expander is mechanically oscillated when the piezo device is turned on. In detail, the bone expander is configured such that a body 222 is of a flare shape in which a diameter increases from an upper outer face toward a lower outer face, and a head 224 is formed on the body 222 and is of a round shape R for preventing the maxillary membrane 16 from being damaged when coming into contact with the membrane for maxillary sinus lift.

Further, the whole of the outer face of the body 222 is provided with a lattice-type cutting blade 226, and on the upper outer face of the body 222, a water supply hole 228 is formed which branches off at 120° in three directions while extending through a support pole 240, which is formed on a lower portion of the body 222.

Further, a stopper 250 integrally protrudes from the upper outer face of the support pole 240 in order to restrict the insertion depth of the body 222 into the maxillary sinus floor 12 for the expansion of the perforation. Here, if required, the stopper 250 may be formed and used as a separate member without being formed on the support pole 240.

Figure 12:
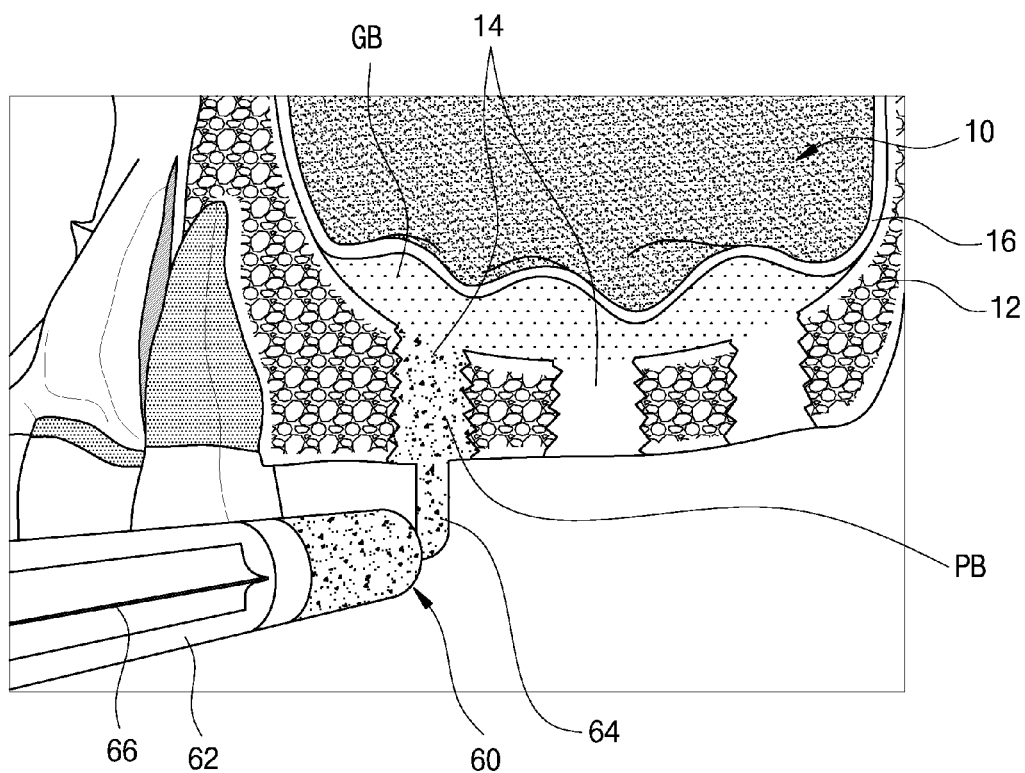
FIG. 12 is a cross-sectional view illustrating the state of inserting granular bone graft material via the vertical hole using the bone infuser.
Figure 13:
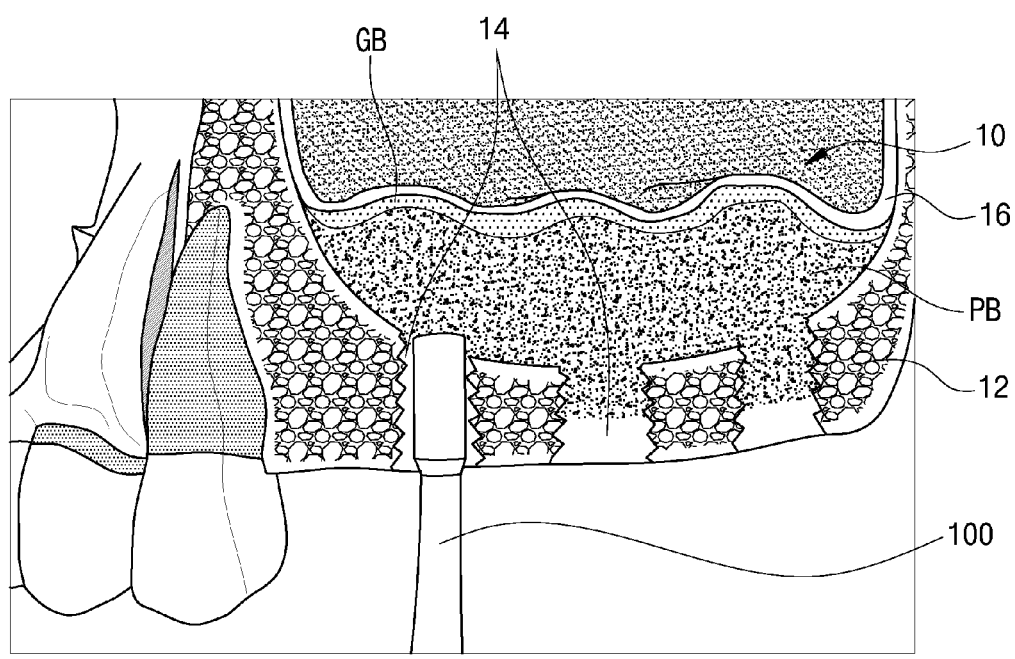
FIG. 13 is a view illustrating the state of pushing the granular bone graft material, which has been inserted via the vertical hole, using the condenser.
Figure 14:
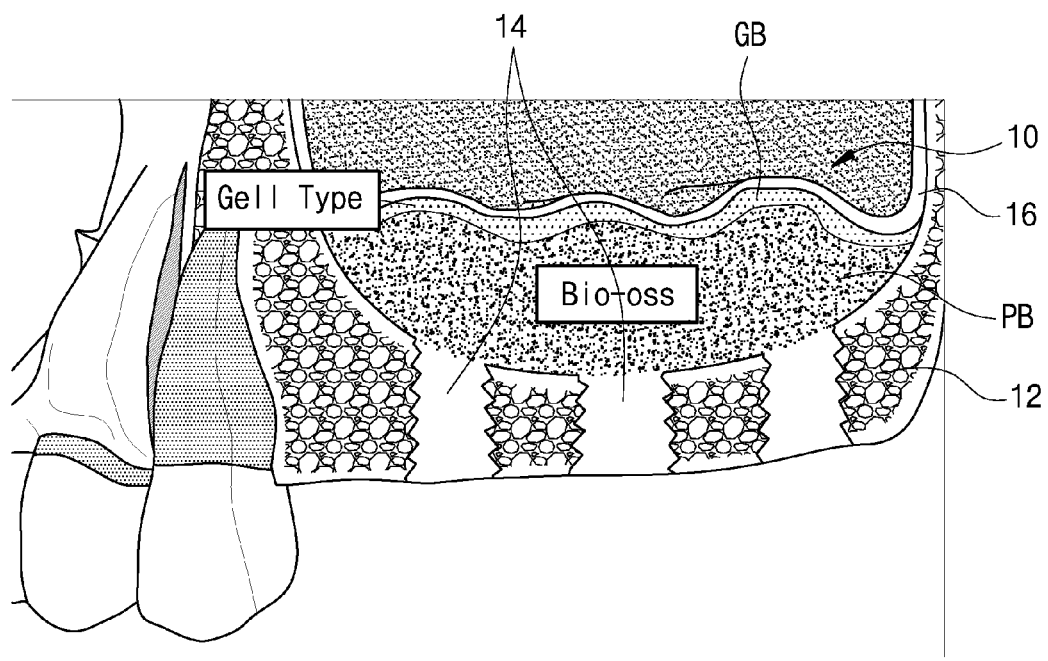
FIG. 14 is a cross-sectional view illustrating the state of having completed the process of bone grafting for thickening the maxillary sinus floor before the placement of an implant.

Next, in the fourth step, as shown in FIG. 12, a bone infuser 60, in which granular bone graft material PB is filled in a syringe barrel, is inserted via the vertical hole 14 of the maxillary sinus floor 12, and as a piston 66 is pushed into the syringe barrel, the granular bone graft material PB is injected while pushing up the gel type bone graft material GB infused in the gap of the maxillary membrane 16. In the fifth step, as shown in FIG. 13, a condenser 100 is inserted via the vertical hole 14 so as to push the granular bone graft material PB up to a position where an upper end of the vertical hole 14 is closed and then cure the same.

In the case of the conventional operating method, since the granular bone graft material PB is injected into the vertical hole having a narrow diameter just after drilling the maxillary sinus floor 12, the coarse particles of the granular bone graft material conglomerate, insertion takes a long time, and the bone grafting done with a quantity of bone is difficult to implement.

However, according to the bone graft method of the present invention, owing to the sufficiently expanded vertical hole 14, a large quantity of fine or even coarse granular bone graft material can be injected quickly. Here, the gel type bone graft material GB, which was already injected, protects the maxillary membrane 16 from the coarse granular bone graft material PB. Further, if the particles of the granular bone graft material conglomerate and are pushed into the maxillary sinus 10 using the condenser 100 as shown in FIG. 13, the gel type bone graft material GB absorbs such a shock so as to effectively protect the maxillary membrane 16.

Figure 15:
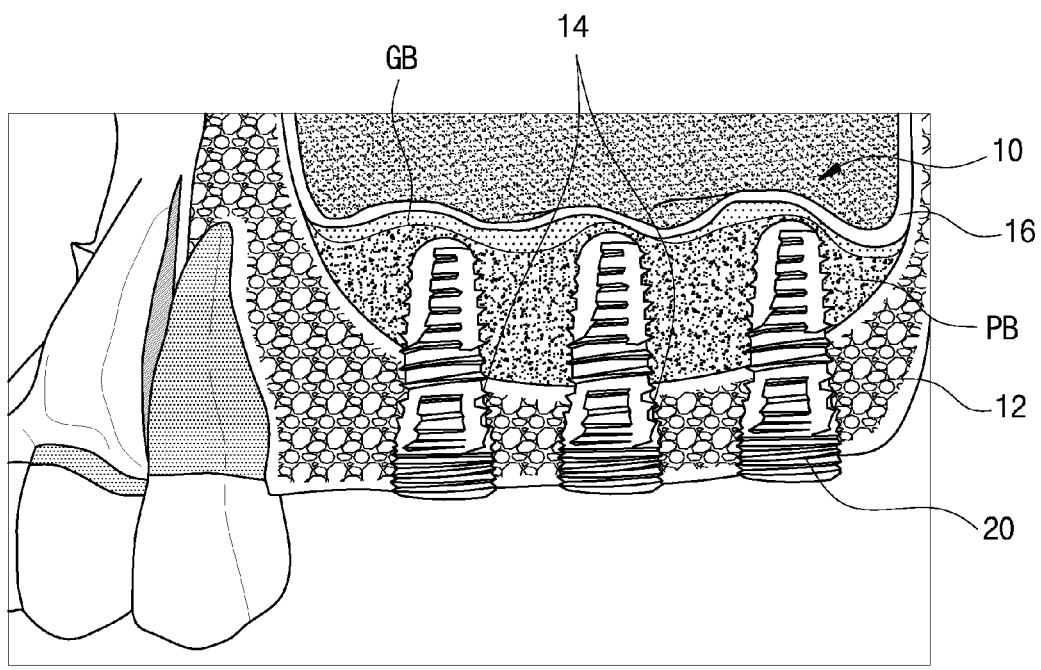
FIG. 15 is a cross-sectional view illustrating the state of having completed the placement of an implant into the vertical hole shown in FIG. 14.

Next, in the sixth step, finally, as shown in FIG. 15, an implant 20 can be placed in the vertical hole 14 in the state where the strong initial stability is secured in the vertical hole.

Form the foregoing, according to the present invention, upon placement of the implant, the vertical hole can be formed and enlarged with ease in the maxillary sinus floor, the maxillary membrane can be easily lifted in an always-stable state using the piezotome and gel type bone graft material while preventing the membrane from becoming damaged, and even the bone graft material of coarse bone meal can be uniformly diffused and infused, thereby ensuring that the implant is placed in a fast, safe manner while allowing a patient to keep relaxed.

Although the preferred embodiments of the method of maxillary sinus bone grafting for implant placement according to the present invention have been described for illustrative purposes, those skilled in the art will appreciate that various modifications, additions and substitutions are possible, without departing from the scope and spirit of the invention as disclosed in the accompanying claims. Thus, it should be understood that the present invention includes all such modifications, additions and substitutions.

What is claimed is:

1. A method of maxillary sinus bone grafting for placement of an implant, the method comprising:
   a first step of forming a vertical hole in a maxillary sinus floor of a maxillary sinus for placement of the implant;
   a second step of lifting a maxillary membrane via the vertical hole in the maxillary sinus floor;
   a third step of enlarging a diameter of the vertical hole with the maxillary membrane lifted;
   a fourth step of inserting the bone graft material via the enlarged vertical hole;
   a fifth step of pushing the inserted bone graft material in a space between the maxillary sinus floor and the maxillary membrane; and a sixth step of after the bone graft material has been cured, placing the implant into the vertical hole;

wherein the second step includes a first sub-step of primarily lifting the maxillary membrane via the vertical hole of the maxillary sinus floor and a second sub-step of filling gel type bone graft material between the maxillary sinus floor and the maxillary membrane, which has been primarily lifted via the vertical hole of the maxillary sinus floor, so as to secondarily lift the maxillary membrane.

2. The method according to claim 1, wherein in the first step, the maxillary sinus floor is drilled using first and second bone compactors in turn.

3. The method according to claim 2, wherein the first and second bone compactors are of a diameter of 2.0 mm and 3.0 mm, respectively.

4. The method according to claim 1, wherein in the first sub-step, the lifting is carried out using a piezotome, wherein the maxillary membrane is lifted by means of the pressure of water fed via the center of the piezotome.

5. The method according to claim 4, wherein the piezotome is provided on an outer circumference of a piezo pole thereof with a protruding stopper for restricting an insertion distance depending on a thickness of the maxillary sinus floor, so as to upon lifting, prevent a tip of the piezotome from excessively pushing up and damaging the maxillary membrane when being inserted into the maxillary sinus.

6. The method according to claim 1, wherein in the second sub-step, the lifting is carried out using a bone infuser, first and second infuser bodies of which are detachably screwed in turn onto a leading end of a syringe barrel and which pushes the gel type bone graft material, which is filled in the bone infuser, between the maxillary sinus floor and the primarily lifted maxillary membrane so as to secondarily lift the maxillary membrane.

7. The method according to claim 1, wherein in the third step, third to fifth bone compactors are used to enlarge the vertical hole.

8. The method according to claim 7, wherein the third to fifth bone compactors are of a diameter of 3.8 mm, 4.0 mm, and 5.0 mm, respectively.

9. The method according to claim 1, wherein in the fourth step, the inserting is carried out using a bone infuser, first and second infuser bodies of which are detachably screwed in turn onto a leading end of a syringe barrel and which inserts granular bone graft material, which is filled in the bone infuser.

10. The method according to claim 9, wherein in the fifth step, the granular bone graft material is pushed up to an upper end of the vertical hole using a condenser.

11. The method according to claim 1, wherein the granular bone graft material is of coarse or fine particles.

* * * * *